(12) United States Patent
Davis et al.

(10) Patent No.: US 10,830,727 B2
(45) Date of Patent: *Nov. 10, 2020

(54) ELECTRODE AND USE THEREOF

(71) Applicants: Oxford University Innovation Limited, Oxfordshire (GB); Universidade Estadual Paulista "Julio de Mesquita Filho", San Paulo (BR)

(72) Inventors: Jason Davis, Oxford (GB); Paulo Roberto Bueno, Sao Paulo (BR)

(73) Assignees: Universidade Estadual Paulista "Julio de Mequita Filho", Centro (BR); Oxford University Innovation Limited, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/803,267

(22) Filed: Nov. 3, 2017

(65) Prior Publication Data
US 2018/0209931 A1  Jul. 26, 2018

Related U.S. Application Data

(63) Continuation of application No. 14/398,208, filed as application No. PCT/GB2013/051121 on May 1, 2013, now Pat. No. 9,810,656.

(30) Foreign Application Priority Data

May 1, 2012 (GB) .................................. 1207585.9

(51) Int. Cl.
G01N 27/327 (2006.01)
G01N 33/543 (2006.01)

(52) U.S. Cl.
CPC ....... *G01N 27/327* (2013.01); *G01N 27/3276* (2013.01); *G01N 33/5438* (2013.01);
(Continued)

(58) Field of Classification Search
CPC .... G01N 27/327–3272; G01N 27/3276–3278; G01N 33/48; G01N 33/487; G01N 33/50; G01N 2800/00–385
See application file for complete search history.

(56) References Cited

U.S. PATENT DOCUMENTS

| | | | |
|---|---|---|---|
| 5,003,065 A | 3/1991 | Merritt et al. | |
| 9,810,656 B2* | 11/2017 | Davis | G01N 33/5438 |
| 2012/0264144 A1* | 10/2012 | Jose | C07K 17/06 |
| | | | 435/7.92 |

FOREIGN PATENT DOCUMENTS

| | | |
|---|---|---|
| EP | 1379684 A2 | 1/2004 |
| WO | 2005001122 A2 | 1/2005 |
| WO | 2011069997 A2 | 6/2011 |

OTHER PUBLICATIONS

Tajima et al, "Significance of antibody orientation unravelled: Well-oriented antibodies recorded high binding affinity", Anal Chem, Feb. 2011, 83(6), 1969-1976.
(Continued)

*Primary Examiner* — Alexander S Noguerola
(74) *Attorney, Agent, or Firm* — Banner & Witcoff, Ltd.

(57) ABSTRACT

The application relates to an electrode for use in the electrochemical detection of a target species, wherein the electrode has a planar surface disposed on which are probe molecules that are capable of binding selectively to the target species, wherein the electrode, prior to binding of the probe molecules with the target species, has an electron transfer resistance per area of the electrode of from 10 megaohms cm$^{-2}$ to 95 megaohms cm$^{-2}$.

16 Claims, 8 Drawing Sheets

(52) U.S. Cl.
CPC .. *G01N 2333/00* (2013.01); *G01N 2333/4737* (2013.01); *G01N 2800/00* (2013.01)

(56) References Cited

OTHER PUBLICATIONS

Chen et al, "Electrochemical Impedance Immunosensor based on Three-Dimensionally ordered macroporous gold film", Anal Chem, 2008, 80, 2133-2140.

Hennessey et al, "Electrochemical investigations of the interaction of C-reactive protein (CRP) with a CRP antibody chemically immobilised on a gold surface", Analytica Chimica Acta 643, 2009, 45-53.

Albrecht et al, "Two immunoassay formats for fully automated CRP detection in human serum". Analytical and Bioanalytical Chemistry 2008, 391: 1845-1852.

Balkenhohl et al, "Screen-printed electrodes as impedimetric immunosensors for the detection of anti-transglutaminase antibodies in human sera", Analytica Chimica Acta, 2007a, 597: 50-57.

Balkenhohl et al, An impedimetric immunosensor for the detection of autoantibodies directed against gliadins. Analyst 2007b, 132: 314-322.

Bogomolova et al, "Challenges of Electrochemical Impedance Spectroscopy in Protein Biosensing" Analytical Chemistry, 2009, 81, 3944-3949.

Buch et al, "An Electrochemical Immunosensor for C-Reactive Protein Based on Multi-Walled Carbon Nanotube-Modified Electrodes" Electroanalysis 2008, 20, 2592-2594.

Centi et al, "Detection of C Reactive Protein (CRP) in Serum by an Electrochemical Aptamer-Based Sandwich Assay", Electroanalysis 2009, 21: 1309-1315.

Cho HY, et al. "Synthesis of Biocompatible PEG-Based Star Polymers with Cationic and Degradable Core for siRNA Delivery", Biomacromolecules 2011, 12: 3478-3486.

Gabay C et al, "Mechanisms of disease: Acute-phase proteins and other systemic responses to inflammation", New England Journal of Medicine 1999, 340: 448-454.

Harder et al, "Molecular conformation in oligo(ethylene glycol)-terminated self-assembled monolayers on gold and silver surfaces determines their ability to resist protein adsorption", Journal of Physical Chemistry B, 1998, 102: 426-436.

Hoogvliet et al, "Electrochemical pretreatment of polycrystalline gold electrodes to produce a reproducible surface roughness for self assembly: A study in phosphate buffer pH 7.4", Analytical Chemistry, 2000. 72: 2016-2021.

Hu et al, "Immunodetection of pentamer and modified C-reactive protein using surface plasmon resonance biosensing", Biosensors & Bioelectronics 2006, 21: 1631-1637.

Kim et al, "Development of indirect-competitive quartz crystal microbalance immunosensor for C-reactive protein", Sensors and Actuators B-Chemical 2009. 143: 444-448.

Klapshina et al, "Novel PEG-organized biocompatible fluorescent nanoparticles doped with an ytterbium cyanoporphyrazine complex for biophotonic applications". Chemical Communications 2010. 46: 8398-8400.

Kushner et al,. "Is high-sensitivity C-reactive protein an effective screening test for cardiovascular risk?" Archives of Internal Medicine 2002, 162: 867-869.

Lee et al, "An integrated microfluidic system for fast, automatic detection of C-reactive protein". Sensors and Actuators B-Chemical 2011, 157: 710-721.

May et al,. "Evaluating the role of biomarkers for cardiovascular risk prediction: focus on CRP, BNP and urinary microalbumin". Expert Review of Molecular Diagnostics 2007, 7: 793-804.

Meyer et al, "SPR-based immunosensor for the CRP detection—A new method to detect a well known protein". Biosensors & Bioelectronics 2006, 21: 1987-1990.

Miller et al, "Use of BNP and CRP as biomarkers in assessing cardiovascular disease: Diagnosis versus risk". Current Vascular Pharmacology 2007, 5: 15-25.

Motie et al, "Binding of model soluble immune complexes to modified C-reactive protein". Journal of Immunology 1996, 156: 4435-4441.

Mygind et al, "The influence of statin treatment on the inflammatory biomarkers YKL-40 and HsCRP in patients with stable coronary artery disease". Inflammation Research 2011, 60: 281-287.

Pai et al, "C-Reactive Protein (CRP) Gene Polymorphisms, CRP Levels, and Risk of Incident Coronary Heart Disease in Two Nested Case-Control Studies". Plos One 3, 2008.

Pan et al, "Electrochemical immunosensor detection of urinary lactoferrin in clinical samples for urinary tract infection diagnosis". Biosensors & Bioelectronics 2010, 26: 649-654.

Pearson et al, "CDC/AHA Workshop on Markers of Inflammation and Cardiovascular Disease—Application to Clinical and Public Health Practice—Overview". Circulation 2004, 110: E543-E544.

Qureshi et al, "Label-free RNA aptamer-based capacitive biosensor for the detection of C-reactive protein". Physical Chemistry Chemical Physics 2010, 12: 9176-9182.

Roberts et al, "Evaluation of four automated high-sensitivity C-reactive protein methods: Implications for clinical and epidemiological applications". Clinical Chemistry 2000, 46: 461-468.

Roberts et al, "Evaluation of nine automated high-sensitivity c-reactive protein methods: Implications for clinical and epidemiological applications. Part 2". Clinical Chemistry 2001, 47: 418-425.

Rodriguez et al, "Aptamer biosensor for label-free impedance spectroscopy detection of proteins based on recognition-induced switching of the surface charge". Chemical Communications 2005.: 4267-4269.

Rosales-Rivera et al, "Electrochemical immunosensor detection of antigliadin antibodies from real human serum". Biosensors & Bioelectronics 2011, 26: 4471-4476.

Schilp et al, "Physicochemical Properties of (Ethylene Glycol)-Containing Self-Assembled Monolayers Relevant for Protein and Algal Cell Resistance". Langmuir 2009, 25: 10077-10082.

Tran et al, "Nanocrystalline diamond impedimetric aptasensor for the label-free detection of human IgE". Biosensors & Bioelectronics 2011, 26: 2987-2993.

Vermeeren et al, "Impedimetric, diamond-based immmunosensor for the detection of C-reactive protein". Sensors and Actuators B-Chemical 2011, 157: 130-138.

Vikholm-Lundin et al, Site-directed immobilisation of antibody fragments for detection of C-reactive protein. Biosensors & Bioelectronics 2006, 21: 1141-1148.

Vyas et al, "Modifying Randles Circuit for Analysis of Polyoxometalate Layer-by-Layer Films". Journal of Physical Chemistry B 2010, 114: 15818-15824.

Wee et al, "Novel electrical detection of label-free disease marker proteins using piezoresistive self-sensing micro-cantilevers". Biosensors & Bioelectronics 2005, 20: 1932-1938.

A. Johnson et al., 'Sensitive Affimer and Antibody Based Impedimetric Label-Free Assays for C-reactive Protein' Analytical Chemistry, vol. 84, Jul. 10, 2012, 6553-6560.

Th. Bryan et al., 'An Optimised Electrochemical Biosensor for the Label-Free Detection of C-reactive Protein in Blood' Biosensors and Bioelectronics, vol. 39, No. 1, Jan. 15, 2013, 94-98.

J. Y. Park et al., 'Label-Free Detection of Antibody-Antigen Interactions on (R)-Lipo-diaza-18-crown-6 Self-Assembled Monolayer Modified Gold Electrodes' Analytical Chemistry, vol. 80, 2008, 4686-4993.

Aug. 30, 2012—(GB) Search Report—App No. GB1207585.9—3 pages.

Jul. 18, 2013—(WO) International Search Report and Written Opinion—App. No. PCT/GB2013/051121—14 pages.

Wu et al., "Development of an enrofloxacin immunosensor based on label-free electrochemical impedance spectroscopy," Talanta 79 (2009) pp. 62-67.

(56) References Cited

OTHER PUBLICATIONS

Wutz et al., "Simultaneous determination of four different antibiotic residues in honey by chemiluminescence multianalyte chip immunoassays," Microchim Acta, Jan. 29, 2011, 9 pages.

* cited by examiner

ELECTRODE AND USE THEREOF

CROSS REFERENCE TO RELATED APPLICATIONS

This application is a continuation of U.S. application Ser. No. 14/398,208, filed Oct. 31, 2014, which is a National Stage Application under 35 U.S.C. 371 of co-pending PCT application number PCT/GB2013/051121, filed 1 May 2013; which claims priority to GB1207585.9, filed 1 May 2012, each of which are hereby incorporated by reference in their entireties for any and all non-limiting purposes.

FIELD OF THE INVENTION

The present invention relates to an electrode for use in the electrochemical detection of target species, including, but not limited to, C-reactive protein.

BACKGROUND

C-reactive protein (CRP) is an acute-phase protein synthesized by the liver, widely accepted as a biomarker for cardiovascular disease and inflammation (May and Wang 2007, Miller et al. 2007, Mygind et al. 2011, Pai et al. 2008). Generally, levels in plasma are less than 2.0 mg/L for healthy individuals (Vikholm-Lundin and Albers 2006), but increase up to 1000 fold during an acute phase of inflammation (Gabay and Kushner 1999). The American Heart Association and the United States Centre for Disease Control have suggested three categories of CRP concentration for the evaluation of cardiovascular disease risk: a CRP concentration below 1.0 mg/L representing low risk, a 1.0 to 3.0 mg/L range average risk, and levels above 3.0 mg/L representing high risk (Kushner and Sehgal 2002, Lee et al. 2011). The reliable and early quantification of this target if often, then, cited as a means of improving the outcome of cardiovascular or inflammatory disease through appropriate intervention or treatment.

Currently, a number of CRP testing methods are available in clinical laboratories using turbidimetric and nephelometric technologies (Roberts et al. 2000, Roberts et al. 2001), or human CRP enzyme-linked immunosorbent assay (ELISA) kits. However, these methods are generally not suitable for the clinical practice as they are either not sensitive enough, time-consuming, prone to false negatives or cost-ineffective (Pearson et al. 2004). CRP quantification methods based on surface plasmon resonance (SPR) (Hu et al. 2006, Meyer et al. 2006), piezoelectric microcantilevers (Wee et al. 2005), quartz crystal microbalance technology (Kim et al. 2009), microfluidics (Lee et al. 2011) and electrochemistry (Buch and Rishpon 2008, Centi et al. 2009), have been developed during the past few years. Among these, electrochemical assays promise most in terms of low cost, flexibility and sensitivity. Electrochemical impedance spectroscopy (EIS), in particular, can sensitively monitor the changes in capacitance or charge-transfer resistance associated with material binding at specifically prepared receptive electrode surfaces and requires no prior labelling (Bogomolova et al. 2009, Rodriguez et al. 2005). In recent years a number of CRP assays by EIS have been reported. To date, however, these have been either of limited sensitivity (Vermeeren et al. 2011), not demonstrably specific (Hennessey et al. 2009), or to not encompass a clinically relevant range (Chen et al. 2008, Qureshi et al. 2010).

This subject-matter of this application relates to the development of a robust and highly sensitive assay for CRP in whole and dilute blood serum across the entire clinically relevant range. The technique can also be applied to other markers. The interfaces are readily prepared, exhibit very good selectivity and are re-useable after assay with no apparent loss of sensitivity. We have, additionally, considered the importance of receptive layer initial resistance in subsequently observed sensitivity and demonstrated not only a clear correlation but also an ability to tune, and therefore optimise, receptive film characteristics.

SUMMARY OF THE INVENTION

Figure 1:
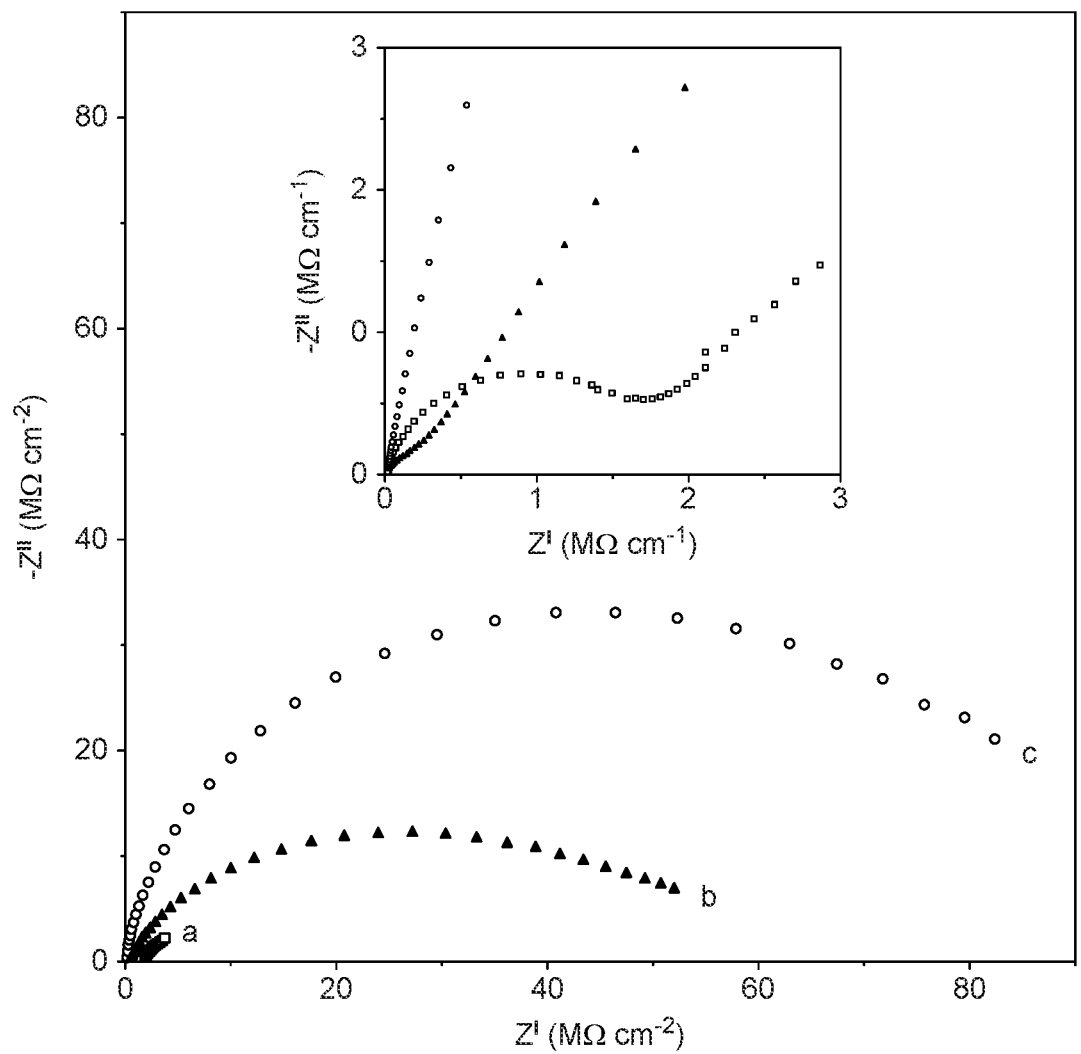
FIG. 1 shows Nyquist plots of different electrodes recorded in PBST (10 mM, pH 7.4) solution containing 1.0 mM $Fe(CN)_6^{3-/4-}$, for (a) bare gold electrode; (b) gold electrode modified with the self-assembled monolayer; and (c) gold electrode with CRP antibody immobilized on the monolayer. The inset magnifies the high frequency region.

In a first aspect, there is provided an electrode for use in the electrochemical detection of a target species, wherein the electrode has a planar surface disposed on which are probe molecules that are capable of binding selectively to the target species, wherein the electrode, prior to binding of the probe molecules with the target species, has an electron transfer resistance per area of the electrode of from 10 megaohms cm$^{-2}$ to 95 megaohms cm$^{-2}$. In an embodiment, the target species is or comprises C-reactive protein and/or the probe molecules comprise antibodies or antibody fragments. The use with other target species and probe molecules is nevertheless described below.

In an embodiment, there is provided an electrode for use in the electrochemical detection of C-reactive protein, wherein the electrode has a planar surface disposed on which are probe molecules that are capable of binding selectively to C-reactive protein, wherein the electrode prior to binding of the probe molecules with C-reactive protein has an electron transfer resistance per area of the electrode of from 10 megaohms cm$^{-2}$ to 95 megaohms cm$^{-2}$ In an embodiment, there is provided an electrode for use in the electrochemical detection of a target species, wherein the electrode has a planar surface disposed on which are probe molecules comprising antibodies or antibody fragments that are capable of binding selectively to the target species, wherein the electrode prior to binding of the probe molecules with the target species has an electron transfer resistance per area of the electrode of from 10 megaohms cm$^{-2}$ to 95 megaohms cm$^{-2}$ In a third aspect, there is provided a method for detecting a target species in an electrochemical impedance spectroscopy technique, wherein the method comprises contacting an electrode defined in the first aspect with a carrier medium comprising the target species, and detecting an electrical signal at the working electrode.

In a third aspect, there is provided an electrochemical impedance spectrometer, wherein the spectrometer comprises an electrode as defined in the first aspect.

In a fourth aspect, there is provided a use of an electrode according to the first aspect or an electrochemical impedance spectrometer according to the third aspect for the detection of a target species.

The present inventors have found that controlling the resistance of an electrode, which is related to the amount of coverage of a probe molecule, before binding to a target can significantly increase the sensitivity of the electrode. It has previously been assumed that increasing the coverage of probe molecules on a surface would increase its sensitivity. However, the present inventors found that keeping the coverage below certain levels (as indicated by initial resistance), increased the sensitivity of the electrode.

DETAILED DESCRIPTION

The present invention provides the first to the fourth aspects described herein. Optional and preferred features will now be described. Any of the features described herein may be combined with any of the other features described herein, unless otherwise stated.

The electrode, prior to binding of the probe molecules with the target species, preferably has an electron transfer resistance per area of the electrode of 95 megaohms cm$^{-2}$ or less. The electrode, prior to binding of the probe molecules with the target species, preferably has an electron transfer resistance per area of the electrode of 10 megaohms cm$^{-2}$ or more. The electrode, prior to binding of the probe molecules with the target species, preferably has an electron transfer resistance per area of the electrode of from 10 megaohms cm$^{-2}$ to 95 megaohms cm$^{-2}$.

Optionally, the electrode, prior to binding of the probe molecules with the target species, has an electron transfer resistance per area of the electrode of from 20 megaohms cm$^{-2}$ to 95 megaohms cm$^{-2}$, optionally an electron transfer resistance per area of the electrode of from 40 megaohms cm$^{-2}$ to 95 megaohms cm$^{-2}$, optionally an electron transfer resistance per area of the electrode of from 50 megaohms cm$^{-2}$ to 95 megaohms cm$^{-2}$, optionally an electron transfer resistance per area of the electrode of from 55 megaohms cm$^{-2}$ to 95 megaohms cm$^{-2}$.

Figure 8:
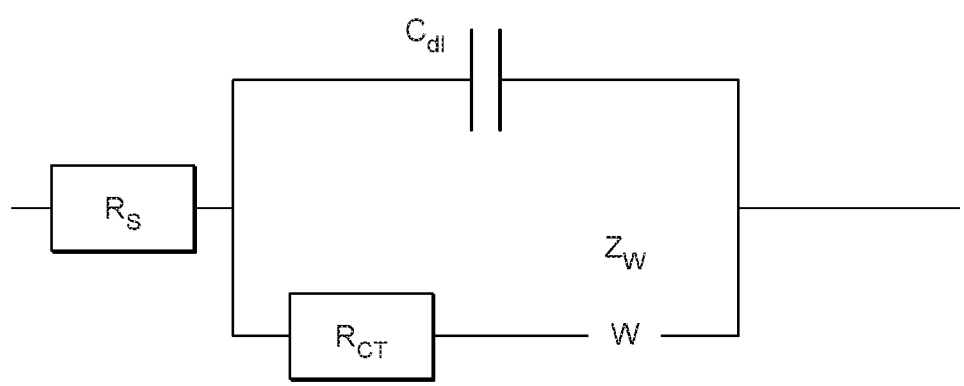
FIG. 8 shows an equivalent circuit model that can be used for data fitting to determine the charge transfer resistance of an electrode as described herein.

Electron transfer resistance, sometimes termed the charge transfer resistance, can be measured using known techniques. In an embodiment, the electron transfer resistance is determined by using an electrochemical impedance spectrometer to obtain impedance information about the electrode, and using an ideal Randles equivalent circuit, which includes the charge transfer resistance as an element of the circuit. Such a Randles equivalent circuit is described, for example, in Vyas R N, Li K Y, Wang B. 2010. Modifying Randles Circuit for Analysis of Polyoxometalate Layer-by-Layer Films. Journal of Physical Chemistry B 114: 15818-15824, which is incorporated herein by reference. An example of an ideal Randles equivalent circuit is illustrated in FIG. 8. In this figure, $R_{ct}$ represents the charge (or electron) transfer resistance, $Z_w$ represents the Warburg impedance, $R_s$ is the solution resistance (sometimes denoted $R_{sol}$), and Cat is the capacitance between the electrode surface and ions in the liquid carrier medium (this is sometimes denoted $C_{surf}$). Fitting impedance data to a circuit to obtain electron (or charge) transfer resistance is known to the skilled person. It is described in many publications, including, but not limited to, Electroanalysis 19, 2007, No. 12, 1239-1257 (an article entitled Label-free Impedance Biosensors: Opportunities and Challenges, authored by Daniels, et al), which is incorporated herein by reference in its entirety, and references cited therein. Commercial software is available for circuit fitting, for example "Fit and Simulation version 1.7" software available from Autolab, The Netherlands, which may accompany a frequency resolved analyser module of an EIS spectrometer (e.g. also available from Autolab, The Netherlands).

The electron transfer resistance per area of the electrode is determined by dividing the charge transfer resistance of the electrode by the area of the electrode (having the probe molecules thereon). This area may be determined using known techniques. In an embodiment, the area of the electrode is the effective surface area of the electrode, which can be calculated by taking the area of a cathodic peak in coulombs and applying the relationship $$A = \frac{Q}{482 \ \mu C \ cm^{-2}},$$

where A is the effective area of the electrode, and Q is the area of the cathodic peak in colombs (see, for example, Hoogvliet, J. C.; Dijksma, M.; Kamp, B.; van Bennekom, W. P. *Anal Chem* 2000, 72, 2016, which is incorporated herein by reference in its entirety), and dividing the charge transfer resistance (Ret) by the effective area.

The electrode may comprise any electrically conducting material. The working electrode may comprising a metal or carbon. The metal may be a metal in elemental form or an alloy of a metal. Optionally, the whole of the electrode comprises a metal or carbon. The electrode may comprise a transition metal. The electrode may comprise a transition metal selected from any of groups 9 to 11 of the Periodic Table. The electrode may comprise a metal selected from, but not limited to, rhenium, iridium, palladium, platinum, copper, indium, rubidium, silver and gold. The electrode may comprise a metal selected from gold, silver and platinum. The electrode may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes.

In a preferred embodiment, the electrode comprises gold.

The surface of the electrode is planar, which includes a generally flat surface, typically without indentations, protrusions and pores. Such electrode surfaces can be prepared, before probe molecules and any associated linker molecules are bound to the surface, by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 µm or less, optionally 5 µm or less, optionally 3 µm or less, optionally 1 µm or less, optionally 0.5 µm or less, optionally 0.1 µm or less. Following polishing, the electrode surface may be washed, e.g. ultrasonically, optionally in a suitable liquid medium, such as water, e.g. for a period of at least 1 minute, e.g. from about 1 minute to 10 minutes. Optionally, the electrode surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the electrodes can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

The probe molecules are capable of binding selectively to a target species, which may be or comprise C-reactive protein. Other target species are described below. The probe molecule preferably comprises a binding species selected from an antibody, an antibody fragment, an aptamer, an oligosaccharide, a peptide, and a protein. Preferably, the probe molecules comprise a binding species selected from one or more of an antibody, a nucleic acid and a peptide. The binding species is capable of binding to the target species, e.g. C-reactive protein. The probe moieties bind selectively to the target species, e.g. C-reactive protein.

If the probe molecules comprise an antibody or an antibody fragment, the antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, and a horse. In an embodiment, the probe molecules comprise an antibody of the IgG type derived from a goat.

If the probe molecules comprise an aptamer, the aptamer may be selected from a peptide aptamer, a DNA aptamer and a RNA aptamer.

The target species may be selected from, but is not limited to, proteins, polypeptides, antibodies, nanoparticles, drugs, toxins, harmful gases, hazardous chemicals, explosives, viral particles, cells, multi-cellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide.

If the target species is or comprise a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. a chemical or biological entity which may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

In a preferred embodiment, the target species is a protein. The method and other aspects of the invention may be used for the detection or identification of a proteins.

The target species may be any antigen or analyte that is indicative of a particular disease. The target may be selected from, for example, C-reactive protein, angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2.

The target species may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the target is glucose, the probe moieties may be selected from, for example, the molecular recognition element of GDH-FAD assay or a glucose/galactose binding protein ("GGBP") (Scholle, et al., Mol. Gen. Genet 208: 247-253 (1987)). If the target is IL-2RA, the probe moieties may comprise or consist of a monoclonal antibody specific for IL-2RA. If the target species is or comprises C-reactive protein, preferably this is human C-reactive protein.

As indicated above, preferably, the probe molecules comprise a binding species selected from one or more of an antibody, a nucleic acid and a peptide. The binding species may be directly attached to the surface of the electrode or attached to the surface of the electrode via a linker species. If a linker species is present on the surface of the electrode, preferably the linker species forms a self-assembling monolayer.

The electrode as described herein may be formed by forming a self-assembling monolayer of linker species, optionally activating the linker species, and then binding the binding species to at least some of the linker species.

Preferably, the electrode surface having the probe molecules thereon, as a whole, is selective for the target species. If the electrode surface having the probe molecules thereon is selective for the target species, this indicates that substantially only or only the target species will bind to the surface (binding to the probe molecules), and other species (e.g. present in the carrier medium with the target species) will not bind, or not bind to any significant degree, to other parts of the electrode surface or other species thereon. For example, the electrode surface may comprise a self-assembling monolayer of linker molecules, some of which are bound to probe moieties, e.g. antibodies, that selectively bind to a target (e.g. C-reactive protein). When in a liquid carrier medium, e.g. blood, the electrode surface preferably only binds to the target species, not to other species present in the liquid carrier medium. Such selective electrode surfaces may be termed highly selective electrode surfaces.

In an embodiment, the probe molecule is of the formula A--L--B, where A is a moiety that binds to the surface of the electrode, L is a linker moiety and B is a moiety which binds to the target species, e.g. C-reactive protein.

'A' may be selected from an appropriate binding group, depending on the nature of the material of the electrode. A may be selected from, but is not limited to, biotin, hydrazine, alkynyl, alkylazide, amino, hydroxyl, carboxy, thio, aldehyde, phosphoinothioester, maleimidyl, succinyl, succinimidyl, isocyanate, ester, strepavidin, avidin, neuavidin, and biotin binding proteins. If the electrode comprises a noble material, e.g. gold, silver or platinum, A is preferably thio, which may be selected from —SH and —S—. If the electrode comprises a metal that has a layer of oxide on its surface, e.g. copper, A may be a carboxy group.

L may be any species that covalently links A with B. L is preferably a species that allows formation of a self-assembling monolayer. L may comprise an alkylene moiety comprising at least 2 carbons, the alkylene moiety being directly attached to A; optionally the alkylene moiety is a straight-chain alkylene moiety. L may comprise an alkylene moiety comprising at least 10 carbons, optionally from 10 to 30 carbons, optionally from 10 to 20 carbons, optionally from 11 to 15 carbon atoms, and the alkylene moiety is optionally a straight-chain alkylene moiety, and the alkylene moiety is directly attached to A.

In an embodiment, L is of the formula —(CH$_2$)$_n$-(—O—CH$_2$—CH$_2$—)$_m$-D-, wherein n is from 1 to 30 and m is from 0 to 10 and D is a group that binds to B. D may be selected from a single bond, —(C=O)—, —OCH$_2$—(C=O)—, —(C=O)—NH—, —(C=O)—O—OCH$_2$—(C=O)—NH—, —OCH$_2$—(C=O)—OH—, —O—, —NH—. n may be from 10 to 20. m may be 1 to 5, optionally 2 to 4, optionally 3. Optionally, if D is any one of the species (C=O)—NH—, —(C=O)—O—OCH$_2$—(C=O)—NH—, —OCH$_2$—(C=O)—O—, —O— and —NH—, then —NH— or —O— in these species may be derived from a probe molecules, e.g. antibody, prior to being bound to the linker species L.

B may be selected from a binding species as described above, for example selected from an antibody, an antibody fragment, an aptamer, an oligosaccharide, a peptide, a protein. Such species that bind selectively to target species, e.g. C-reactive protein, are available commercially, e.g. goat anti-human CRP polyclonal antibody, which is available from AbD Serotec.

In an embodiment, A-L- is a species of the formula thio-(CH$_2$)$_n$-(—O—CH$_2$—CH$_2$—)$_m$-D-, wherein n is from 1 to 30 and m is from 0 to 10 and D is a group that binds to B; optionally n, m and D may be as defined above, and thio is selected from —S— and HS—.

In an embodiment, A-L- is a species of the formula thio-$(CH_2)_n$-$(—O—CH_2—CH_2—)_m$-D-, wherein n is from 1 to 30 and m is from 0 to 10 and D is a group that binds to B; optionally n, m and D may be as defined above, and thio is selected from —S— and HS—.

In an embodiment, A-L- is a species of the formula thio-$(CH_2)_n$-$(—O—CH_2—CH_2—)_m$-D-, wherein n is from 1 to 30 and m is from 0 to 10 and D is a group that binds to B; optionally n, m and D may be as defined above, and thio is selected from —S— and HS—.

B is preferably capable of binding selectively to the target species, e.g. C-reactive protein. B preferably comprises or is a binding species selected from an antibody, an antibody fragment, an aptamer, an oligosaccharide, a peptide, and a protein. B preferably comprises or is a binding species selected from one or more of an antibody, an antibody fragment, a nucleic acid and a peptide. Preferably, the probe moieties bind selectively to C-reactive protein.

If B comprises or is an antibody or an antibody fragment, the antibody or the antibody fragment may be selected from one or more of the classes IgA, IgD, IgE, IgG and IgM. The antibody or antibody fragment preferably binds selectively to C-reactive protein.

If B comprises or is an aptamer, the aptamer may be selected from a peptide aptamer, a DNA aptamer and a RNA aptamer.

In an embodiment, an electrode as described herein, e.g. having probe molecules thereon, may be produced by providing the electrode having the planar surface, then forming a self-assembling monolayer of linker species on the planar surface, and attaching probe moieties, e.g. antibodies, that bind to the target species to at least some of the linker species. The linker species may optionally be activated, e.g. by reaction with an activator, such as N-hydroxysuccinimde (NHS), to allow for facile attachment of the probe moieties to the linker species. In an embodiment, the linker species forming the self-assembling monolayer are of the formula A--L, wherein A is a moiety that binds to the surface of the electrode, L is a linker moiety capable of binding to a moiety (which may be denoted B) which binds to the target species, e.g. an antibody. In an embodiment, a may be as defined above, and the linker species L forming the monolayer, prior to binding to the probe moieties, is of the formula —$(CH_2)_n$-$(—O—CH_2—CH_2—)_m$-D-, wherein n is from 1 to 30 and m is from 0 to 10 and D is a group that binds to B. D may be selected from a single bond, —(C=O)—H, —(C=O)OH—OCH$_2$—(C=O)H, —OCH$_2$—(C=O)OH, —(C=O)—NHH, —OCH$_2$—(C=O)—NH$_2$, —OCH$_2$—(C=O)—OH, —OH, —NH$_2$.

The present application also relates to a method for detecting a target species (including, but not limited to, C-reactive protein) in an electrochemical impedance spectroscopy technique, wherein the method comprises contacting an electrode defined in the first aspect with a carrier medium comprising the target species (including, but not limited to, C-reactive protein), and detecting an electrical signal at the working electrode.

Electrochemical impedance spectroscopy (EIS) is known to the skilled person. Generally, a varying ac potential is applied on a bias (or DC) potential between a working electrode and a counter electrode. Generally, EIS involves scanning across a range of ac frequencies. The ratio of the input signal (typically the varying potential) to the output signal (typically the varying current) allows the impedance to be calculated. There is generally a phase difference between the input signal and the output signal, such that the impedance can be considered as a complex function, having a real part (sometimes termed Z') and an imaginary part (sometimes termed Z"). The real and imaginary parts of impedance can be plotted against one another, e.g. in the form of a Nyquist plot, as illustrated in FIG. 1. By fitting the impedance data to an assumed equivalent circuit, the electron transfer resistance can be determined. In the present application, as mentioned above, an ideal Randles equivalent circuit can be used to determine the electron transfer resistance. The frequency range of the varying ac potential applied may be from 0.05 Hz to 10 kHz. The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV. The bias potential (or direct current potential) may be set at any desired potential. If a redox probe is present in the carrier medium, the bias potential may be set at the electrode potential of the redox probe under the conditions at which the method is carrier out.

A redox probe may be present in the carrier medium. The redox probe may be a transition metal species, wherein the transition metal can adopt two valence states (e.g. a metal ion (M) being able to adopt M(II) and M(III) states). In an embodiment, the redox probe contains a metal ion, wherein the metal of the metal ion is selected from iron, ruthenium, iridium, osmium, cobalt, tungsten and molybdenum. In an embodiment, the redox probe is selected from $Fe(CN)_6^{3-/4-}$, $Fe(NH_3)_6^{3+/2+}$, $Fe(phen)_3^{3+/2+}$, $Fe(bipy)_2^{3+/2+}$, $Fe(bipy)_3^{3+/2+}$, $Ru^{3+/2+}$, $RuO_4^{3-/2-}$, $Ru(CN)_6^{3-/4-}$, $Ru(NH_3)_6^{3+/2+}$, $Ru(en)_3^{3+/2+}$, $Ru(NH_3)_5(Py)^{3+/2+}$, $Ir^{4+/3+}$, $Ir(Cl)_6^{2-/3-}$, $Ir(Br)_6^{2-/3-}$, $Os(bipy)_2^{3+/2+}$, $Os(bipy)_3^{3+/2+}$, $OxCl_6^{2-/3-}$, $Co(NH_3)_6^{3+/2+}$, $W(CN)_6^{3-/4-}$, $Mo(CN)_6^{3-/4-}$, optionally substituted ferrocene, polyferrocene, quiniones, such as p-benzoquinone and hydroquinone and phenol In an embodiment, the redox probe is an iron-containing species in which iron is in Fe(II) and/or Fe(III) states. In an embodiment, the redox probe is $Fe(CN)_6^{3-/4-}$. The redox probe may be present in the carrier medium an amount of from 0.1 mM to 100 mM, optionally from 0.5 mM to 10 mM, optionally from 0.5 mM to 2 mM, optionally from 0.5 mM to 1.5 mM, optionally about 1 mM.

The carrier medium is preferably in liquid form. The carrier liquid may be any liquid in which the target species (including, but not limited to, C-reactive protein) can be suspended or dissolved. In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid, although additives such as a redox probe, may be present in the undiluted biological fluid. The biological fluid may be selected from blood, urine, tears, saliva, sweat, and cerebrospinal fluid.

Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alkanol, e.g. ethanol. The carrier medium may further comprise a buffer. The buffer may comprise a phosphate.

The method may comprise calculating the concentration of the target species (e.g. C-reactive protein) from the electrical signal. The electrical signal may be converted into impedance data and then converted to the concentration of the target species (e.g. C-reactive protein) from the electrical signal. The electrical signal may be converted into charge transfer resistance data and then converted to the concentration of the target species (e.g. C-reactive protein) from the electrical signal. The method may involve comparing the data obtained in the electrochemical impedance spectroscopy technique, e.g. from the electrical signal, the impedance data or the charge transfer resistance data, and comparing the data with data obtained in a calibration step, to obtain the concentration of the target species (e.g. C-reactive protein). The method may involve an initial calibration step that determines a relationship between the concentration of the target species (e.g. C-reactive protein) and electrochemical data obtained from the electrochemical signal in the electrochemical impedance spectroscopy technique; the electrochemical data may be selected from impedance data and charge transfer resistance data; the relationship may be used to convert the electrochemical data obtained from a sample of interest in the electrochemical impedance spectroscopy technique to the concentration of the target species (e.g. C-reactive protein) in the sample.

The concentration of the target species (e.g. C-reactive protein) in the carrier medium may be 0.1 nM or more, optionally 0.16 nM or more, optionally 0.2 nM or more, optionally 0.5 nM or more. The concentration of the target species (e.g. C-reactive protein) in the carrier medium may be 100 nM or less, optionally 80 nM or less, optionally 50 nM or less, optionally 10 nM or less. The concentration of the target species (e.g. C-reactive protein) in the carrier medium may be from 0.1 nM to 100 nM, optionally from 0.16 nM to 100 nM, optionally from 0.16 nM to 50 nM.

The concentration of the target species (e.g. C-reactive protein) in the carrier medium may be 10 μg/L or more, optionally 15 μg/L or more, optionally 19 μg/L or more, optionally 20 μg/L or more, optionally 0.1 mg/L or more, optionally 1 mg/L or more, optionally 3 mg or more. The concentration of the target species (e.g. C-reactive protein) in the carrier medium may be 100 mg/L or less, optionally 80 mg/L or less, optionally 50 mg/L or less, optionally 30 mg/L or less. The concentration of the target species (e.g. C-reactive protein) in the carrier medium may be from 10 μg/L to 100 mg/L, optionally from 19 μg/L to 100 mg/L, optionally from 19 μg/L to 50 mg/L.

The calculating may comprise one or more comparisons of the electrical signal with the electrical signal of an ideal equivalent circuit.

The present inventors have found that they can regenerate the electrode, that has been bound to target species (e.g. C-reactive protein), by dissociating bound target species (e.g. C-reactive protein) from the electrode. The method may involve, after the contacting of the electrode with the target species (e.g. C-reactive protein), such that the target species (e.g. C-reactive protein) is bound to the probe molecules, and detecting the electrical signal, dissociating the target species (e.g. C-reactive protein) from the probe molecules. The dissociating may comprise contacting of the electrode surface having target species (e.g. C-reactive protein) thereon with an alkali liquid medium, e.g. an alkali aqueous liquid medium, optionally having a pH of 8 or more, optionally a pH of 9 or more, optionally a pH of 10 or more, optionally a pH of 11 or more, optionally a pH of 8 to 12, optionally a pH of 9 to 12. The alkali liquid medium may contain a basic substance. The basic substance is preferably soluble in water. The basic substance may be selected from, but not limited to, a metal hydroxide, a metal carbonate, ammonia. The metal of the metal hydroxide or metal carbonate may be selected from Group 1 and Group 2 of the Periodic Table.

The present invention also relates to an electrochemical impedance spectrometer, wherein the spectrometer comprises an electrode as defined herein. The electrochemical impedance spectrometer may be of a standard design. The electrochemical impedance spectrometer may comprise an electrode of the first aspect as a working electrode, a counter electrode, and, if desired a reference electrode. The electrochemical impedance spectrometer preferably comprises a means for applying, controlling and varying a potential between the working and counter electrodes, and a means for measuring the resultant current. The electrochemical impedance spectrometer preferably comprises a potentiostat for controlling the potential and measuring the resultant current. The electrochemical impedance spectrometer preferably comprises a means for calculating impedance data from the potential applied and the resultant current. The electrochemical impedance spectrometer may comprise a means for calculating electron transfer resistance of the working electrode.

The present invention also relates to the use of an electrode as described herein or an electrochemical impedance spectrometer as described herein for the detection of a target species, e.g. C-reactive protein. The use may include detecting the presence of and/or detecting the concentration of the target species, e.g. C-reactive protein.

Examples

In the examples below, human CRP, human blood serum and bovine serum albumin (BSA) were purchased from Sigma Aldrich. The goat anti-human CRP polyclonal antibody was purchased from AbD Serotec. 1-ethyl-3-(3-dimethylaminopropyl) carbodiimide (EDC) and N-hydroxysuccinimide (NHS) were purchased from Sigma Aldrich. Polyethylene glycol (PEG) thiol $HS-C_{11}-(EG)_3-OCH_2-COOH$ was purchased from Prochimia Surfaces, Poland. Ultrapure water (18.2 MΩ/cm) was obtained from a Milli-Q system and used throughout. Phosphate buffered saline (PBS) with Tween-20 (PBST, 10 mM, pH 7.4) was prepared by dissolving PBS tablets (Sigma Aldrich) in water with 0.2% v/v Tween-20 added, and filtered using a 0.22 μm membrane filter. All other chemicals were of analytical grade.

2.2. Apparatus

Electrochemical experiments were performed on an Autolab Potentiostat 12 equipped with an FRA2 module (Metrohm Autolab B.V.). A conventional three-electrode system with a gold disk working electrode (1.6 mm diameter, BASi), platinum wire counter electrode and a silver/silver chloride (Ag/AgCl) reference electrode (CH Instruments) were used. All potentials are reported relative to this reference. CRP stock solution concentrations were calculated via the UV absorbance at 280 nm (Motie et al. 1996) using a Shimadzu UV spectrometer (Shimadzu Scientific Instruments).

2.3. Surface Preparation

Gold electrodes were firstly polished with 3.0, 1.0 and 0.1 μm diamond spray (Kemet International Ltd) in sequence and ultrasonically washed in water for about 5 min prior to immersion in freshly prepared piranha solution (concentrated $H_2SO_4$: $H_2O_2$, v/v 3:1. Caution: this must be handled with extreme care!) for 15 min. Electrodes were then electrochemically polished by potential cycling (CV) between −0.1 and 1.25 V until a stable reduction peak was obtained. The effective surface area of the gold electrode can be calculated at this point by taking the area of the cathodic peak in coulombs and applying the relationship $$A = \frac{Q}{482 \ \mu C \ cm^{-2}}$$

(Hoogvliet et al. 2000), and the reported charge transfer resistance ($R_{ct}$) was normalized by this.

(1) Hoogvliet, J. C.; Dijksma, M.; Kamp, B.; van Bennekom, W. P. *Anal Chem* 2000, 72, 2016.

Figure 7:
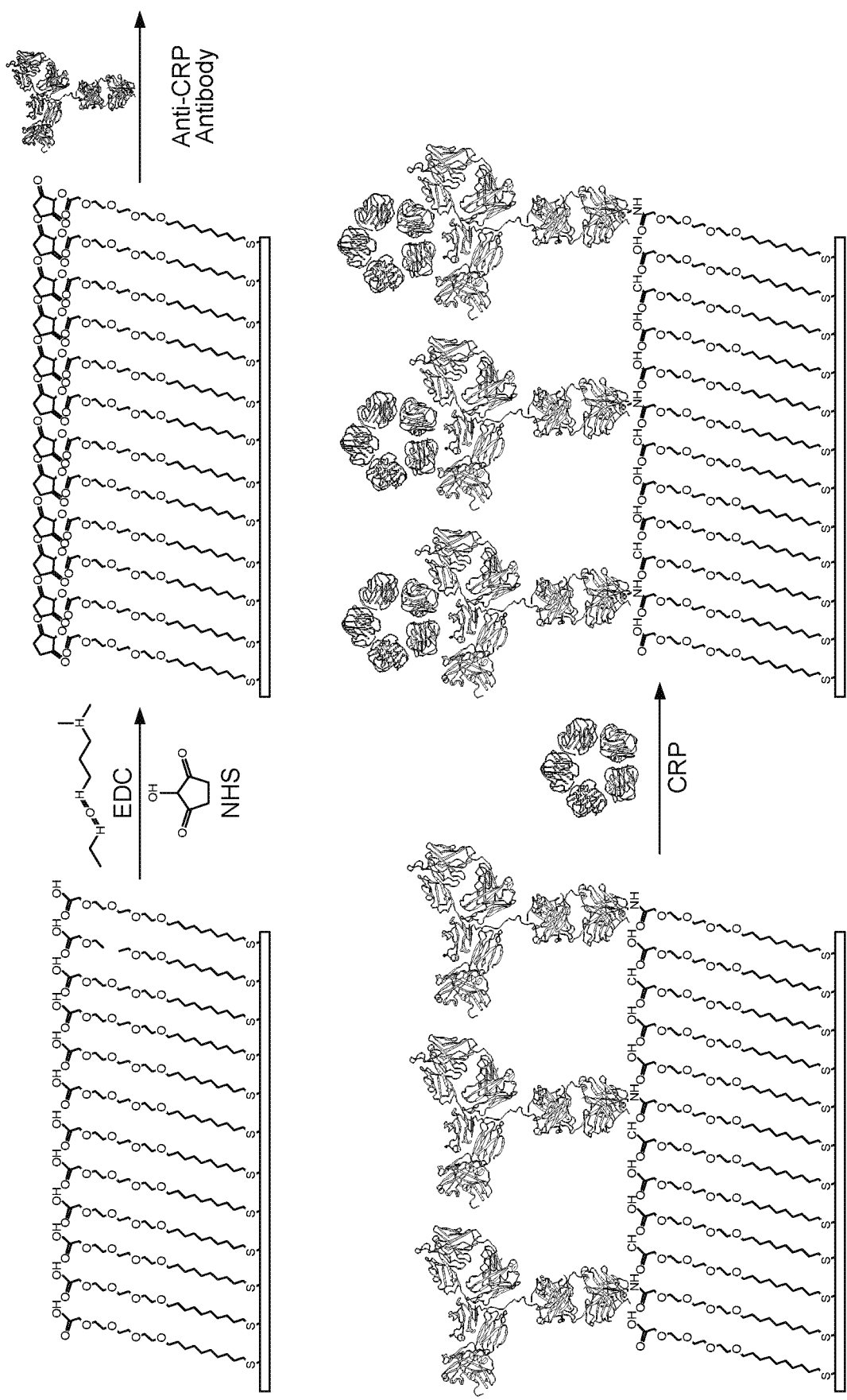
FIG. 7 is a schematic illustration of the stepwise fabrication of CRP responsive EIS interfaces.

Pre-treated gold electrodes were then dried in a flow of nitrogen gas and immediately immersed in a 10 mM solution of HS—$C_{11}H_{22}$-(EG)$_3$-OCH$_2$—COOH in ethanol for 16 hours at room temperature. The biocompatible (Cho et al. 2011, Klapshina et al. 2010) and antifouling properties (Harder et al. 1998, Schilp et al. 2009) of such films are sufficient to enable specific assessments to be made in complex biological fluid. After SAM formation gold surfaces were rinsed with ethanol then water and dried in a flow of nitrogen gas prior to incubation in a solution containing 0.4 M EDC and 0.1 M NHS for 15 minutes (terminal carboxyl group activation) and then 10 µM CRP antibody solution (PBST, pH 7.4) for 1 hour (FIG. 7), unless stated otherwise.

2.4. Electrochemical Impedance Spectroscopy

EIS spectra were recorded across a 0.05 Hz to 10 kHz frequency range. The amplitude of the applied sine wave potential was 10 mV with the direct current potential set at 0.25 V (the $E_0$ of the redox probe used, 1.0 mM Fe(CN)$_6^{3-/4-}$). Data was acquired in 10 mM PBST solution, plotted in the form of complex plane diagrams (Nyquist plots), and fitted through an ideal Randles equivalent circuit (Vyas et al. 2010), as illustrated in FIG. 8. In this figure, $R_{ct}$ represents the charge (or electron) transfer resistance, $Z_w$ represents the Warburg impedance, $R_s$ is the solution resistance, and Cal is the capacitance between the electrode surface and target species or ions in the liquid carrier medium. The raw impedance data is acquired by a FRA (frequency resolved analyser) module (in this case manufactured by Autolab, The Netherlands), then fit to the equivalent circuit in FIG. 8 using inbuilt software ("Fit and Simulation version 1.7"). The software runs multiple iterations of fittings to reduce errors then outputs values for all equivalent circuit components, including Rct.

Assays were carried out by electrode incubation in CRP spiked PBST, specific dilutions of blood serum or whole blood serum at room temperature for 30 min each. In the first two cases PBST was pre-doped with redox probe. EIS responses were normally recorded in the same incubation solution, with the exception of the whole (undiluted) blood serum tests, where the electrodes were rinsed with PBST after incubation prior to assessment in PBST containing 1.0 mM Fe(CN)$_6^{3-/4-}$. To initially evaluate interfacial selectivity BSA was used. Used surfaces were regenerated using 6 mM NaOH and 0.6% ethanol for 5 min (Albrecht et al. 2008) prior to PBST washing.

3. Results and Discussion 3.1. Biosensor Fabrication and Initial Impedance

EIS presents a useful means of characterising the stepwise fabrication of a receptive surface. In Nyquist plots, the semicircles at low sampling frequency report on charge transfer restrictions imposed sterically or electrostatically as films are constructed. Predictably, there are sharp increases in $R_{CT}$ as the receptor layer is fabricated. $R_{ct}$ specifically increases from less than 4.5 kΩ/cm$^2$ to ~45 MΩ/cm$^2$ after the formation of the PEG SAM and further upwards on antibody immobilisation (FIG. 1). The resistance of the interface thereafter responds in a calibratable manner to target protein binding.

Figure 2A:
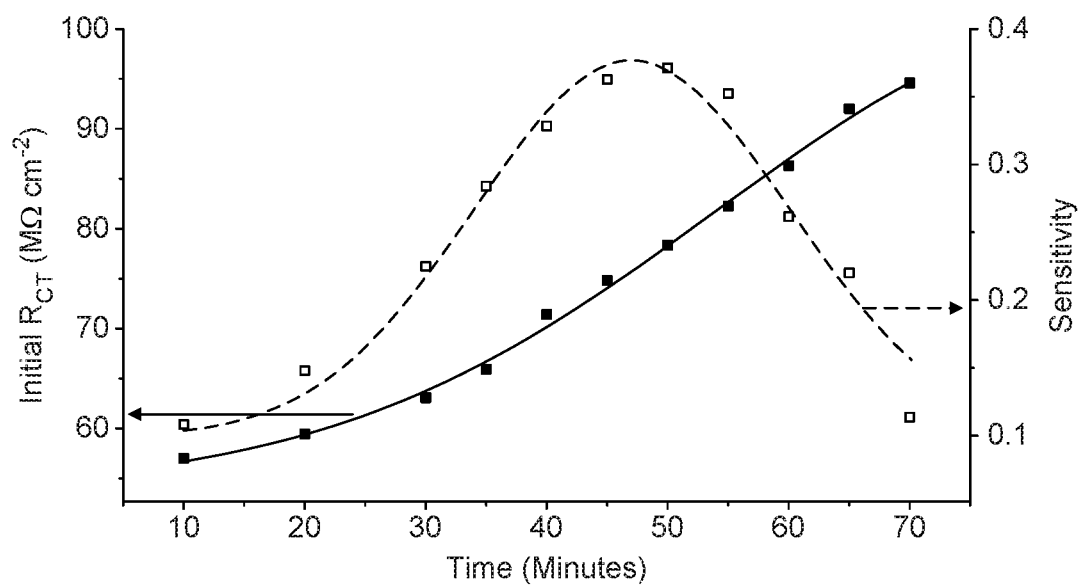
FIG. 2A is a graph showing the effect of CRP antibody immobilization time on the initial charge transfer resistance, $R_{ct}$ and sensitivity of the biosensor (the sensitivity was determined as change in $R_{ct}$ divided by the initial $R_{ct}$)
Figure 2B:
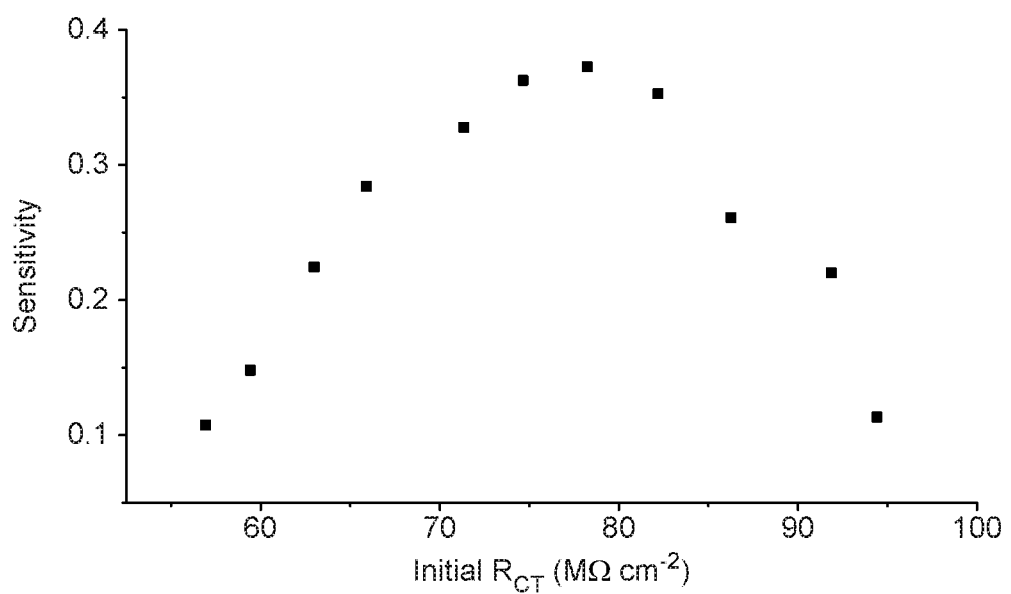
FIG. 2B is a graph illustrating the relationship between the initial $R_{CT}$ and the sensitivity.

The present inventors found that the initial resistance of an electrode, i.e. before binding to CRP, plays a role in subsequently observed sensitivity. This initial resistance is directly tuneable through the antibody surface density. This is itself controllable through either incubation time or incubation concentration as the layer is constructed. FIGS. 2A-2B summarise the observed trend in assay sensitivity with initial layer charge transfer resistance. Notably, as the antibody surface coverage decreases (as the immobilization timeframe is reduced from 70 min to 10 min), assay sensitivity initially increases in magnitude by up to 400% (and the limit of detection decreases consequently) before falling presumably as the density of surface bound and functional antibodies falls below the point where specific target binding is effective (in terms of probability). These observations are robust and reproducible across numerous assays.

3.2. Detection of CRP in Buffer

Figure 3A:
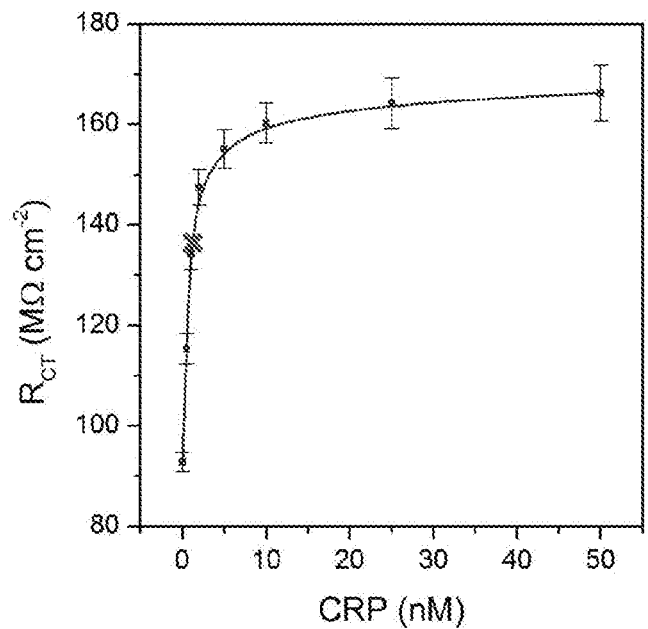
FIG. 3A is a graph showing the recorded charge-transfer resistance ($R_{ct}$) of the biosensor after the incubation with different concentrations of CRP protein in PBST (10 mM, pH 7.4) containing 1.0 mM $Fe(CN)_6^{3-/4-}$.
Figure 3B:
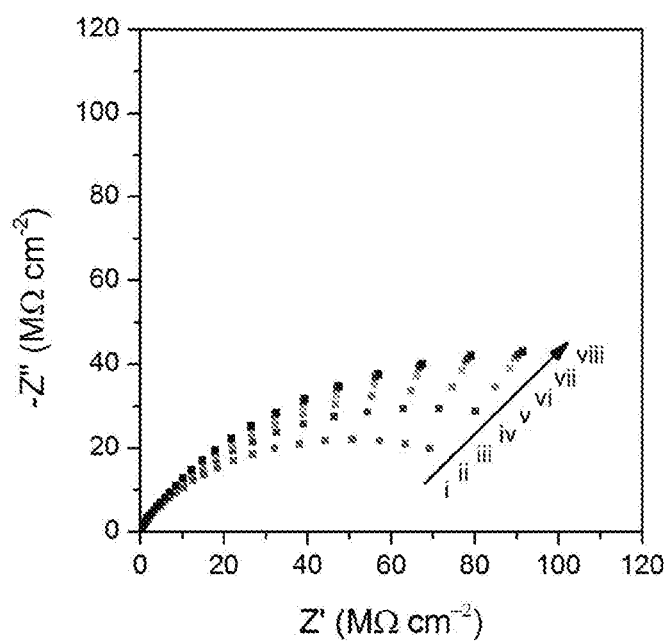
FIG. 3B is a graph showing Faradaic impedance spectra corresponding to the biosensor after the incubation in PBST solution with different CRP concentrations (curves i to viii represent 0, 0.5, 1.0, 2.0, 5.0, 10, 25, and 50 nM CRP, respectively).

The prepared interfaces were subsequently used to screen CRP in PBST. From the progressive and then saturating increases in $R_{CT}$ with concentration (FIGS. 3A-3B), a dissociation constant $K_D$ of 1.1±0.11 nM, can be derived, a value in excellent agreement with a previous differential pulse voltammetry determination with the same polyclonal antibody (Hennessey et al. 2009).

Prior to saturation, $R_{CT}$ reports linearly with logarithmic sensitivity on CRP concentration across a 0.5-50 nM range (equivalent to 60 µg/L to 6.0 mg/L) with a limit of detection (LOD) of 176±18 pM. This low detection limit (equating to ~19 µg/L) confirms sensitivity to be comfortably sufficient for practical application and is married to a assay range encompassing that which is clinically relevant. This range, taken with its associated detection limit, exceeds the clinical relevance of any prior reported CRP assay to the best of our knowledge. The prepared interfaces are, additionally, unresponsive (<3% change in signal) to BSA levels of up to 100 nM.

3.3. Detection of CRP in the Blood Serum

From a point of care perspective, the direct and facile assessment of CRP in blood serum is necessary. In any label free assay, however, this is exceedingly demanding. Though a number of amperometric or sandwich based EIS immunoassay methods have been demonstrated (Balkenhohl and Lisdat 2007a, b, Pan et al. 2010, Rosales-Rivera et al. 2011, Tran et al. 2011), to the best of our knowledge, there exists no prior report of a non-amplified and label free impedance assays that has been reported as being effective in undiluted complex biological media.

Figure 4A:
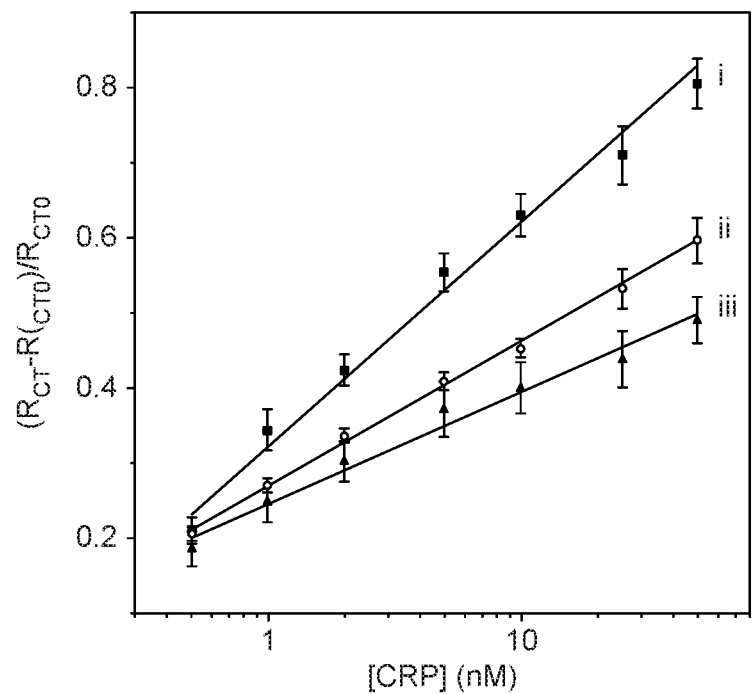
FIG. 4A is a graph showing calibration curves for the CRP biosensors performed in different solutions, namely:
  (i) PBST (10 mM, pH 7.4) with 1.0 mM $Fe(CN)_6^{3-/4-}$;
  (ii) PBST (10 mM, pH 7.4) with 1.0 mM $Fe(CN)_6^{3-/4-}$ and 10% human blood serum; and
  (iii) PBST (10 mM, pH 7.4) with 1.0 mM $Fe(CN)_6^{3-/4-}$ and 20% human blood serum.
Figure 4B:
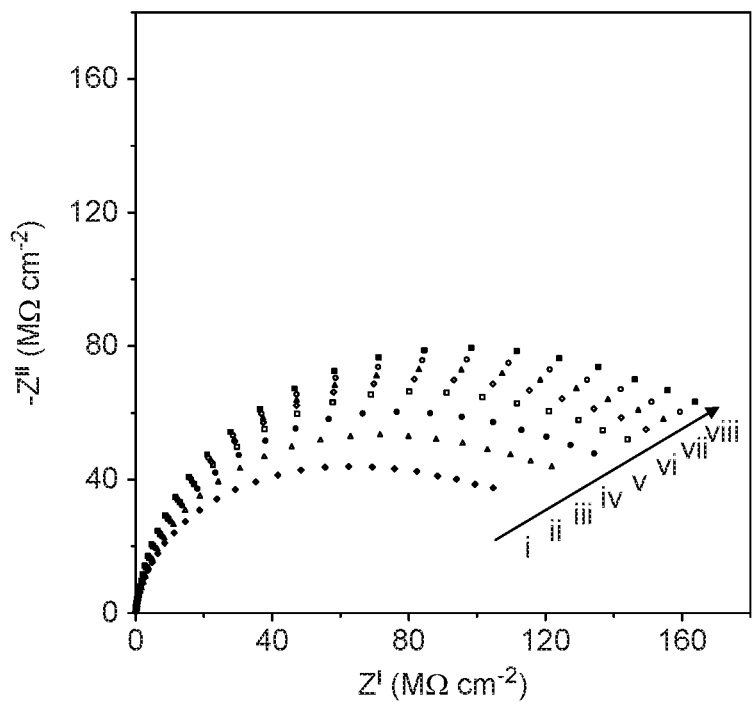
FIG. 4B is a graph showing Faradaic impedance spectra corresponding to the biosensor after the incubation in PBST solution containing 1.0 mM $Fe(CN)_6^{3-/4-}$ and 10% human blood serum, with different CRP concentrations (curves i to viii represent 0, 0.5, 1.0, 2.0, 5.0, 10, 25, and 50 nM CRP, respectively).
Figure 5:
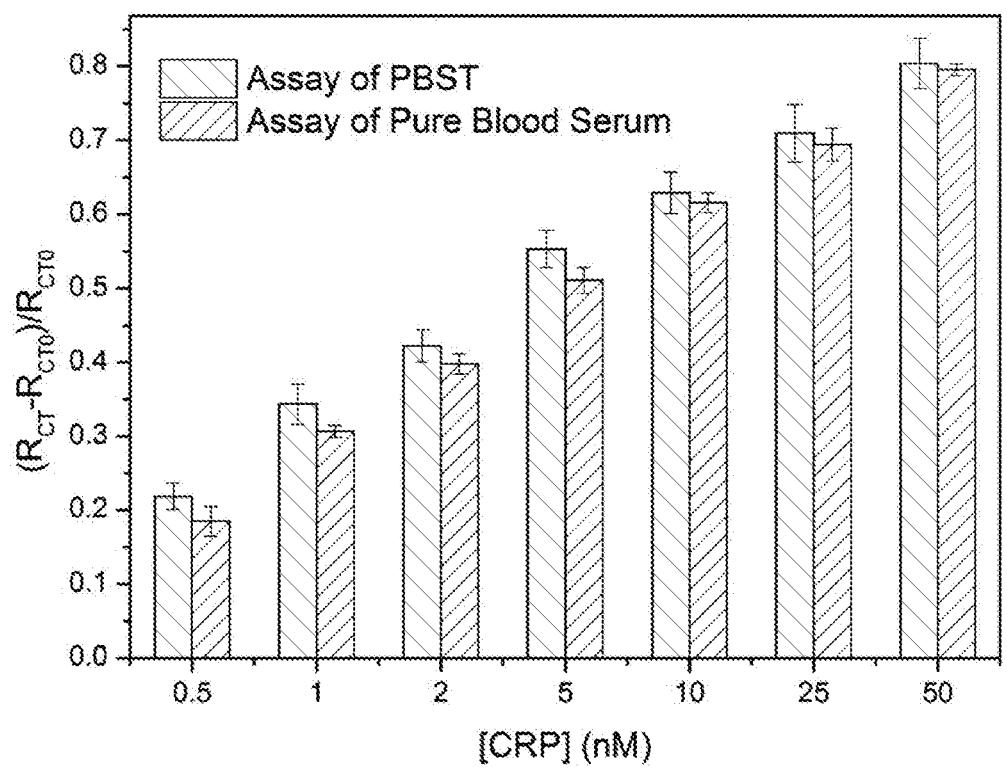
FIG. 5 shows a comparison of biosensor assays of CRP in buffer solution and pure blood serum. Biosensors were incubated in CRP spiked buffer solution and pure blood serum, respectively, and impedance analyses carried out in PBST solution containing 1.0 mM $Fe(CN)_6^{3-/4-}$. Impedance levels of CRP free buffer or pure blood serum were taken as background.

Being confident about the degree of control we had over our electrode interfaces and in the light of the low levels of response to even high levels of BSA, we screened here for CRP in blood serum in two ways. In the first instance, in situ assessments were made with CRP spiked blood serum at controllable dilution in PBST (FIGS. 4A-4B). Under such circumstances reliable linear assessments were possible across the clinically relevant range with an LOD of 262±28 pM at serum concentrations of up to 10% v/v.

Subsequent analyses were carried out with CRP spiked undiluted blood serum; Resistance optimized sensor electrodes were incubated in these solutions for 15 minutes and then measured after rinsing with PBST. As is evident in FIG.

5, the sensor response in such analyses is markedly close (in the higher concentration range of most clinical relevance, 10-50 nM, the differences are <3%) to that observed in spiked PBST. This enables analysis to be performed in whole blood serum across the CRP concentration range required for useful cardiovascular disease risk assessment. From a practical perspective, these assays can be carried out with as little as 5 µL of undiluted blood serum and report quantitatively within 10 min. The utilised electrode interfaces are also, subsequently, reusable (see below).

3.4. Biosensor Regeneration

Figure 6:
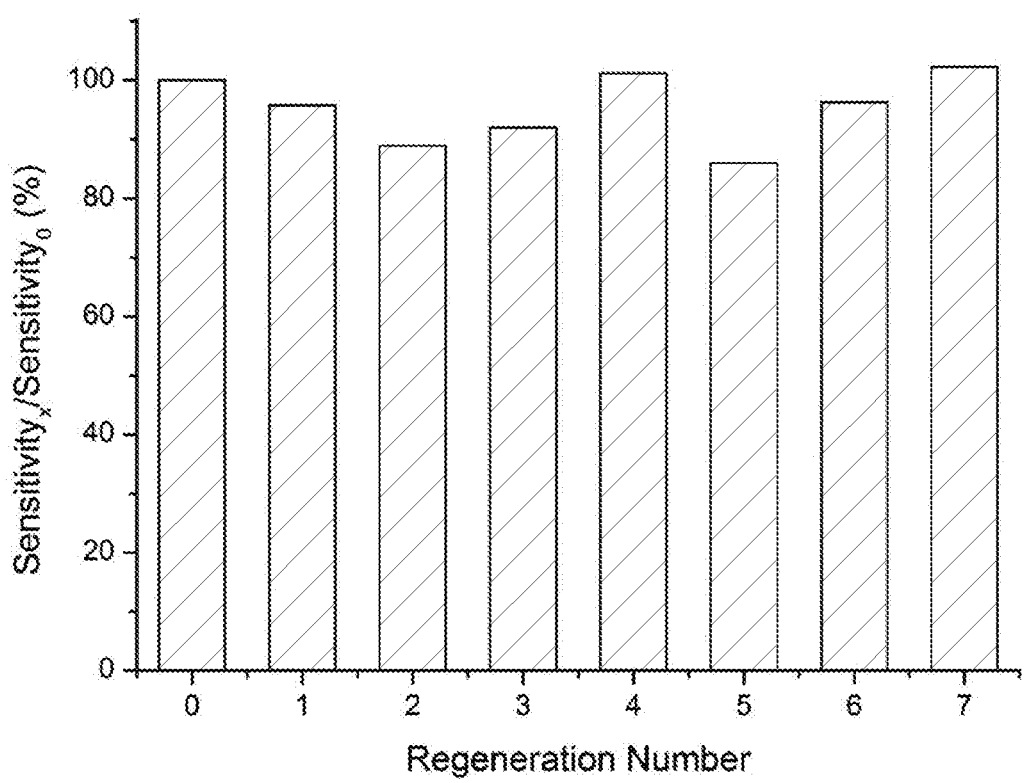
FIG. 6 shows the regeneration of the CRP biosensor. The biosensor was regenerated by immersing the electrode in 6 mM NaOH and 0.6% ethanol for 5 min and then washed with PBST, and the impedance measurements were taken in a solution containing PBST (10 mM, pH 7.4), 1.0 mM $Fe(CN)_6^{3-/4-}$ and 10% human blood serum.

Surface regeneration was achieved with high fidelity (see FIG. 6) by immersion of used surfaces in 6 mM NaOH and 0.6% ethanol for 5 min (to disassociate the CRP antibody-antigen complex) and then washing with PBST. We believe the robust regeneration is possible partially because of the absence of the BSA passivation commonly employed at such immunoassaying surfaces. The interfaces herein could be reused without significant detriment of the assay (97% of the original interface response retained over 7 regenerations). This regeneration is effective for assays carried out in PBS, diluted serum or whole serum.

The present inventors have found an optimised and reusable electrochemical label free biosensor capable of the reliable detection of CRP across the clinically relevant range in dilute or whole blood serum. The in situ determined polyclonal antibody binding affinity maps very well onto previous determinations at comparable interfaces. In addition to facilitating high assay sensitivity and selectivity, the prepared biosensor interfaces also exhibited satisfying reusability. In optimising the initial interfacial resistance through antibody surface density, assay sensitivity can be markedly increased.

Assays such as these are easily integrated into portable and multiplexed formats capable of sampling just a few µL of biological fluid within minutes. We believe the presented results serve as an important basis for the development of convenient point of care analysis of a marker (i.e. CRP) long considered as a sensitive probe of infection, trauma, inflammation and cardiac risk.

REFERENCES

Albrecht C, Kaeppel N, Gauglitz G. 2008. Two immunoassay formats for fully automated CRP detection in human serum. Analytical and Bioanalytical Chemistry 391: 1845-1852.

Balkenhohl T, Lisdat F. 2007a. Screen-printed electrodes as impedimetric immunosensors for the detection of anti-transglutaminase antibodies in human sera. Analytica Chimica Acta 597: 50-57.

Balkenhohl T, Lisdat F. 2007b. An impedimetric immunosensor for the detection of autoantibodies directed against gliadins. Analyst 132: 314-322.

Bogomolova A, Komarova E, Reber K, Gerasimov T, Yavuz O, Bhatt S, Aldissi M. 2009. Challenges of Electrochemical Impedance Spectroscopy in Protein Biosensing. Analytical Chemistry 81: 3944-3949.

Buch M, Rishpon J. 2008. An Electrochemical Immunosensor for C-Reactive Protein Based on Multi-Walled Carbon Nanotube-Modified Electrodes. Electroanalysis 20: 2592-2594.

Centi S, Sanmartin L B, Tombelli S, Palchetti I, Mascini M. 2009. Detection of C Reactive Protein (CRP) in Serum by an Electrochemical Aptamer-Based Sandwich Assay. Electroanalysis 21: 1309-1315.

Chen X J, Wang Y Y, Zhou J J, Yan W, Li X H, Zhu J J. 2008. Electrochemical impedance immunosensor based on three-dimensionally ordered macroporous gold film. Analytical Chemistry 80: 2133-2140.

Cho H Y, et al. 2011. Synthesis of Biocompatible PEG-Based Star Polymers with Cationic and Degradable Core for siRNA Delivery. Biomacromolecules 12: 3478-3486.

Gabay C, Kushner I. 1999. Mechanisms of disease: Acute-phase proteins and other systemic responses to inflammation. New England Journal of Medicine 340: 448-454.

Harder P, Grunze M, Dahint R, Whitesides G M, Laibinis P E. 1998. Molecular conformation in oligo(ethylene glycol)-terminated self-assembled monolayers on gold and silver surfaces determines their ability to resist protein adsorption. Journal of Physical Chemistry B 102: 426-436.

Hennessey H, Afara N, Omanovic S, Padjen A L. 2009. Electrochemical investigations of the interaction of C-reactive protein (CRP) with a CRP antibody chemically immobilized on a gold surface. Analytica Chimica Acta 643: 45-53.

Hoogvliet J C, Dijksma M, Kamp B, van Bennekom W P. 2000. Electrochemical pretreatment of polycrystalline gold electrodes to produce a reproducible surface roughness for self assembly: A study in phosphate buffer pH 7.4. Analytical Chemistry 72: 2016-2021.

Hu W P, Hsu H Y, Chiou A, Tseng K Y, Lin H Y, Chang G L, Chen S J. 2006. Immunodetection of pentamer and modified C-reactive protein using surface plasmon resonance biosensing. Biosensors & Bioelectronics 21: 1631-1637.

Kim N, Kim D K, Cho Y J. 2009. Development of indirect-competitive quartz crystal microbalance immunosensor for C-reactive protein. Sensors and Actuators B-Chemical 143: 444-448.

Klapshina L G, Douglas W E, Grigoryev I S, Ladilina E Y, Shirmanova M V, Mysyagin S A, Balalaeva I V, Zagaynova E V. 2010. Novel PEG-organized biocompatible fluorescent nanoparticles doped with an ytterbium cyanoporphyrazine complex for biophotonic applications. Chemical Communications 46: 8398-8400.

Kushner I, Sehgal A R. 2002. Is high-sensitivity C-reactive protein an effective screening test for cardiovascular risk? Archives of Internal Medicine 162: 867-869.

Lee W B, Chen Y H, Lin H I, Shiesh S C, Lee G B. 2011. An integrated microfluidic system for fast, automatic detection of C-reactive protein. Sensors and Actuators B-Chemical 157: 710-721.

May A, Wang T J. 2007. Evaluating the role of biomarkers for cardiovascular risk prediction: focus on CRP, BNP and urinary microalbumin. Expert Review of Molecular Diagnostics 7: 793-804.

Meyer M H F, Hartmann M, Keusgen M. 2006. SPR-based immunosensor for the CRP detection—A new method to detect a well known protein. Biosensors & Bioelectronics 21: 1987-1990.

Miller V M, Redfield M M, McConnell J P. 2007. Use of BNP and CRP as biomarkers in assessing cardiovascular disease: Diagnosis versus risk. Current Vascular Pharmacology 5: 15-25.

Motie M, Brockmeier S, Potempa L A. 1996. Binding of model soluble immune complexes to modified C-reactive protein. Journal of Immunology 156: 4435-4441.

Mygind N D, Harutyunyan M J, Mathiasen A B, Ripa R S, Thune J J, Gotze J P, Johansen J S, Kastrup J, Grp C T. 2011. The influence of statin treatment on the inflammatory biomarkers YKL-40 and HsCRP in patients with stable coronary artery disease. Inflammation Research 60: 281-287.

Pai J K, Mukamal K J, Rexrode K M, Rimm E B. 2008. C-Reactive Protein (CRP) Gene Polymorphisms, CRP Levels, and Risk of Incident Coronary Heart Disease in Two Nested Case-Control Studies. Plos One 3.

Pan Y, Sonn G A, Sin M L Y, Mach K E, Shih M C, Gau V, Wong P K, Liao J C. 2010. Electrochemical immunosensor detection of urinary lactoferrin in clinical samples for urinary tract infection diagnosis. Biosensors & Bioelectronics 26: 649-654.

Pearson T A, Mensah G A, Hong Y L, Smith S C. 2004. CDC/AHA Workshop on Markers of Inflammation and Cardiovascular Disease—Application to Clinical and Public Health Practice—Overview. Circulation 110: E543-E544.

Qureshi A, Gurbuz Y, Kallempudi S, Niazi J H. 2010. Label-free RNA aptamer-based capacitive biosensor for the detection of C-reactive protein. Physical Chemistry Chemical Physics 12: 9176-9182.

Roberts W L, Sedrick R, Moulton L, Spencer A, Rifai N. 2000. Evaluation of four automated high-sensitivity C-reactive protein methods: Implications for clinical and epidemiological applications. Clinical Chemistry 46: 461-468.

Roberts W L, Moulton L, Law T C, Farrow G, Cooper-Anderson M, Savory J, Rifai N. 2001. Evaluation of nine automated high-sensitivity c-reactive protein methods: Implications for clinical and epidemiological applications. Part 2. Clinical Chemistry 47: 418-425.

Rodriguez M C, Kawde A N, Wang J. 2005. Aptamer biosensor for label-free impedance spectroscopy detection of proteins based on recognition-induced switching of the surface charge. Chemical Communications: 4267-4269.

Rosales-Rivera L C, Acero-Sanchez J L, Lozano-Sanchez P, Katakis I, O'Sullivan C K. 2011. Electrochemical immunosensor detection of antigliadin antibodies from real human serum. Biosensors & Bioelectronics 26: 4471-4476.

Schilp S, Rosenhahn A, Pettitt M E, Bowen J, Callow M E, Callow J A, Grunze M. 2009. Physicochemical Properties of (Ethylene Glycol)-Containing Self-Assembled Monolayers Relevant for Protein and Algal Cell Resistance. Langmuir 25: 10077-10082.

Tran D T, Vermeeren V, Grieten L, Wenmackers S, Wagner P, Pollet J, Janssen K P P, Michiels L, Lammertyn J. 2011. Nanocrystalline diamond impedimetric aptasensor for the label-free detection of human IgE. Biosensors & Bioelectronics 26: 2987-2993. Vermeeren V, Grieten L, Vanden Bon N, Bijnens N, Wenmackers S, Janssens S D, Haenen K, Wagner P, Michiels L. 2011. Impedimetric, diamond-based immunosensor for the detection of C-reactive protein. Sensors and Actuators B-Chemical 157: 130-138.

Vikholm-Lundin I, Albers W M. 2006. Site-directed immobilisation of antibody fragments for detection of C-reactive protein. Biosensors & Bioelectronics 21: 1141-1148.

Vyas R N, Li K Y, Wang B. 2010. Modifying Randles Circuit for Analysis of Polyoxometalate Layer-by-Layer Films. Journal of Physical Chemistry B 114: 15818-15824.

Wee K W, Kang G Y, Park J, Kang J Y, Yoon D S, Park J H, Kim T S. 2005. Novel electrical detection of label-free disease marker proteins using piezoresistive self-sensing micro-cantilevers. Biosensors & Bioelectronics 20: 1932-1938.

We claim:

1. An electrode for use in the electrochemical detection of a target species, the electrode comprising:
   a planar surface having probe molecules disposed thereon, in which the probe molecules are capable of electrochemically detecting a target species by binding selectively to the target species,
   wherein the probe molecule is of the formula A-L-B, where A is a moiety that binds to the surface of the electrode, L is a linker moiety and B is a moiety which binds selectively to the target species;
   wherein the electrode, prior to binding of the probe molecules with the target species, has an electron transfer resistance per area of the electrode of from 10 megaohms cm$^{-2}$ to 95 megaohms cm$^{-2}$, and
   wherein the target species is an antigen or analyte selected from the group consisting of angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, Glade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor; markers useful for diabetes include C-reactive protein; glucose; insulin; TRIG; GPT; HSPA1 B; IGFBP2; LEP; ADIPOQ; CCL2; ENG;
   HP; IL2RA; SCp; SHBG; and TIMP2.

2. An electrode according to claim 1, wherein the probe molecules comprise at least one of: antibodies or antibody fragments.

3. An electrode according to claim 1, wherein the electrode prior to binding of the probe molecules with the target species has an electron transfer resistance per area of the electrode of from 55 megaohms cm$^{-2}$ to 95 megaohms cm'.

4. An electrode for use according to claim 1, wherein the electrode comprises a metal selected from the group consisting of: gold, rhenium, iridium, palladium, platinum, copper, indium, rubidium silver, and combinations thereof.

5. An electrode according to claim 1, wherein A is selected from the group consisting of: biotin, hydrazine, alkynyl, alkylazide, amino, hydroxyl, carboxy, thiol, aldehyde, phosphoinothioester, maleimidyl, succinyl, succinimidyl, isocyanate, ester, strepavidin, avidin, neuavidin, biotin binding proteins, and combinations thereof.

6. An electrode according to claim 1, wherein the probe molecule is of the formula A-L-B, where A is a moiety that binds to the surface of the electrode, L is a linker moiety and B is a moiety which binds selectively to the target species, and L comprises an alkylene moiety comprising at least 10 carbons in which L is of the formula —$(CH_2)_n$-(—O—$CH_2$—$CH_2$—$)_m$-D-, wherein n is from 1 to 30 and m is from 0 to 10 and D is a group that binds to B.

7. An electrode for use in the electrochemical detection of a target species, the electrode comprising:
a planar surface having probe molecules disposed thereon, in which the probe molecules are capable of electrochemically detecting a target species by binding selectively to the target species, wherein the electrode, prior to binding of the probe molecules with the target species, has an electron transfer resistance per area of the electrode of from 10 megaohms $cm^{-2}$ to 95 megaohms $cm^{-2}$,
wherein the target species is an antigen or analyte that is indicative of a particular disease, and
wherein the probe molecule is of the formula A-L-B, where A is a moiety that binds to the surface of the electrode, L is a linker moiety and B is a moiety which binds selectively to the target species, and L comprises an alkylene moiety comprising at least 10 carbons.

8. An electrode according to claim 7, wherein the target species is an antigen or analyte selected from the group consisting of angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1;
insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8;
activin A; leptin (obesity homolog, mouse); plasminogen activator, tissue; proopiomelanocortin (adrenocorticotropin/b eta-lip otropin/alpha-mel anocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, Glade E(nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like; markers useful for diabetes include C-reactive protein; glucose; insulin; TRIG; GPT; HSPA1 B;
IGFBP2; LEP; ADIPOQ; CCL2; ENG; HP; IL2RA; SCp; SHBG; and TIMP2.

9. A method for detecting a target species in an electrochemical impedance spectroscopy technique, wherein the method comprises:
contacting an electrode with a carrier medium comprising a target species in which the electrode comprises a planar surface having probe molecules disposed thereon which are capable of electrochemically detecting the target species via selectively binding to the target species, wherein the electrode, prior to selective binding of the probe molecules with the target species, has an electron transfer resistance per area of the electrode of from 10 megaohms $cm^{-2}$ to 95 megaohms $cm^{-2}$; and
detecting an electrical signal at the electrode to electrochemically detect the target species,
wherein the probe molecule is of the formula A-L-B, where A is a moiety that binds to the surface of the electrode, L is a linker moiety and B is a moiety which binds selectively to the target species,
wherein the target species is an antigen or analyte selected from the group consisting of angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2;
CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, Glade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like; markers useful for diabetes include C-reactive protein; glucose; insulin; TRIG; GPT; HSPA1 B; IGFBP2; LEP; ADIPOQ; CCL2; ENG; HP; IL2RA; SCp; SHBG; and TIMP2.

10. A method according to claim 9, wherein the carrier medium comprises a biological fluid.

11. A method according to claim 10, wherein the biological fluid is selected from the group consisting of: blood, urine, tears, saliva, sweat, cerebrospinal fluid, and combinations thereof.

12. A method according to claim 10, wherein the biological fluid is an undiluted biological fluid.

13. A method according to claim 9, wherein the carrier medium further comprises a redox probe.

14. A method according to claim 9, the method additionally comprising:
   after contacting the electrode with the carrier medium comprising the target species to result in the target species being bound to the probe molecules, dissociating the target species from the probe molecules.

15. A method according to claim 14, the method further comprising:
   after dissociating the target species from the probe molecules, reusing the electrode in an electrochemical method.

16. A method according to claim 9, wherein the method further involves: calculating a concentration of the target species from the electrical signal.

\* \* \* \* \*